US006589989B1

(12) United States Patent
Bollag et al.

(10) Patent No.: US 6,589,989 B1
(45) Date of Patent: Jul. 8, 2003

(54) TREATMENT OF CELL-MEDIATED IMMUNE DISEASES

(75) Inventors: Werner Bollag, Basel (CH); Fritz Ott, Oberrieden (CH)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/485,943

(22) PCT Filed: Aug. 18, 1998

(86) PCT No.: PCT/EP98/05236

§ 371 (c)(1),
(2), (4) Date: Apr. 7, 2000

(87) PCT Pub. No.: WO99/09969

PCT Pub. Date: Mar. 4, 1999

(30) Foreign Application Priority Data

Aug. 23, 1997 (EP) .............................................. 97114651

(51) Int. Cl.$^7$ .............................................. A61K 31/20
(52) U.S. Cl. ...................... 514/559; 514/861
(58) Field of Search ................... 514/559, 861

(56) References Cited

U.S. PATENT DOCUMENTS

| 5,057,501 A | * | 10/1991 | Thornfeldt | 514/53 |
| 5,093,360 A | | 3/1992 | Yu et al. | |
| 5,391,766 A | | 2/1995 | Klaus et al. | |
| 5,428,071 A | | 6/1995 | Bollag et al. | |
| 5,525,635 A | * | 6/1996 | Moberg | 514/588 |
| 5,658,949 A | | 8/1997 | Aggarwal | |
| 5,744,499 A | * | 4/1998 | Quash et al. | 514/639 |
| 5,750,570 A | * | 5/1998 | Voorhees et al. | |
| 5,776,986 A | * | 7/1998 | Couval et al. | 514/698 |
| 5,837,728 A | * | 11/1998 | Purcell | 514/529 |
| 5,932,622 A | * | 8/1999 | Evans et al. | |
| 6,001,885 A | * | 12/1999 | Vega et al. | |
| 6,004,987 A | * | 12/1999 | Demarchez et al. | 514/356 |
| 6,017,960 A | * | 1/2000 | Voorhees et al. | 514/557 |
| 6,083,977 A | * | 7/2000 | Boehm et al. | 514/457 |

FOREIGN PATENT DOCUMENTS

| DE | 4415204 | * | 11/1995 |
| EP | 579 915 | | 1/1994 |
| WO | 9319743 | * | 10/1993 |
| WO | 94/22818 | | 10/1994 |

OTHER PUBLICATIONS

Fujii et al, Metabolic inactivation of retinoic acid . . . , EMBO Journal, 1997, vol. 16/14, pp. 4163–4173.*
Amatruda et al "Retinoids and cells of . . . ", Non–serial–(book–1986): Retinoids and Cell Differentiation., ISBN:0–8493–6322–5.*
Chan et al., N–(4–hydroxyphenyl) retinamide induces . . . , Proc. Annu. Meet. AM. Assc. Cancer Res., 1996, vol. 37, pp. A147.*
Yang et al., Proc. Natl. Acad. Sci. USA, vol. 90, pp. 6170–6174 (Jul. 1993).

* cited by examiner

*Primary Examiner*—William R. A. Jarvis
*Assistant Examiner*—Vickie Kim
(74) *Attorney, Agent, or Firm*—George W. Johnston; Dennis P. Tramaloni; Eileen M. Ebel

(57) ABSTRACT

The invention is related to a method of treating chronic hand eczema in a human patient in need of treatment, using oral administration of 9-cis retinoic acid and pharmaceutically acceptable salts and pharmaceutically acceptable hydrolysable esters thereof, in an effective amount of from 0.05 to 1.5 milligrams per kilogram body weight per day.

8 Claims, No Drawings

TREATMENT OF CELL-MEDIATED IMMUNE DISEASES

This application is a 371 of PCT/EP/98/05236 filed Aug. 18, 1998.

The present invention relates to the use of 9-cis retinoic acid and derivatives or precursors thereof for the manufacture of a medicament for the treatment of T-helper cell type 1 mediated immune diseases as well as to the use of said active substances for the treatment of such diseases.

Despite intensive clinical research with retinoids in the last 27 years, retinoids have not been reported to be clinically useful in the therapy of immunologically mediated diseases. Neither diseases caused by T-helper type-1 cell (Th1) dependent cellular immunity, nor diseases caused by T-helper type-2 cell (Th2) dependent humoral immunity, have been reported to respond to retinoids. As to the classification into Th1 dependent diseases—such as autoimmune and other cell-mediated immune diseases, e.g. rheumatoid arthritis, multiple sclerosis, uveoretinitis, thyreoiditis, Crohn's disease, insulin dependent diabetes mellitus, eczema and systemic lupus erytheematosus, as well as rejection of allogeneic organ transplants—and Th2 dependent diseases—i.e. diseases with dominant humoral or antibody-mediated diseases such as allergic disorders, e.g. atopic dermatitis, allergic rhinitis, hay fever and allergic bronchial asthma—reference is made to Romragnani, ed, Th 1 and Th 2 Cells in Health and Disease. Chem. Immunol., Karger, Basel, 63, pp. 158–170 and 187–203 (1996).

For the first time, quite unexpectedly, it has now been found that a retinoid—namely 9-cis retinoic acid as well as its salts, its esters and its metabolic precursors or prodrugs as well as metabolites of 9-cis retinoic acid, such as 4-oxo-9-cis retinoic acid—is clinically efficacious in the therapy of Th1 dependent diseases.

In the scope of the present invention the term "metabolic precursors and prodrugs as well as metabolites of 9-cis retinoic acid" encompasses compounds that are converted metabolically into 9-cis retinoic acid, and it includes, in particular, 9-cis retinal and 9-cis retinol as well as pharmaceutically acceptable acetals of 9-cis retinal and pharmaceutically acceptable hydrolyzable esters of 9-cis retinol as well as metabolites of 9-cis retinoic acid such as 4-oxo-9-cis retinoic acid or their glucuronides.

In accordance with this invention, it has thus been found that that administration of 9-cis retinoic acid, its pharmaceutically acceptable salts, its pharmaceutically acceptable hydrolyzable esters, 9-cis retinal, its pharmaceutically acceptable acetals, 9-cis retinol and its pharmaceutically acceptable hydrolyzable esters, as well as metabolites of 9-cis retinoic acid, are efficacious in treating patients with T-helper cell type 1 (Th1) mediated diseases.

The invention therefore relates to the use of 9-cis retinoic acid, a pharmaceutically acceptable salt or a pharmaceutically acceptable hydrolyzable ester thereof, 9-cis retinal or a pharmaceutically acceptable acetal thereo: or 9-cis retinol or a pharmaceutically acceptable hydrolyzable ester thereof as well as metabolites of 9-cis retinoic acid for the manufacture of a medicament for the treatment of T-helper cell type 1 (Th1) mediated immune diseases.

The invention also relates to a method for treating patients having T-helper cell type 1 (Th1) mediated immune diseases comprising administering to said human patient a compound selected from the group consisting of 9-cis retinoic acid, pharmaceutically acceptable salts and pharmaceutically acceptable hydrolyzable esters thereof, 9-cis retinal and pharmaceutically acceptable acetals thereof as well as 9-cis retinol and pharmaceutically acceptable hydrolyzable esters thereof as well as metabolites of 9-cis retinoic acid said compound being administered in an amount effective to treat said disease.

In the scope of the present invention, the term "T-helper cell type 1 mediated immune diseases" relates to diseases with dominant cellular immune response, and it encompasses, in particular, autoimmune and other cell-mediated immune diseases, such as rheumatoid arthritis, multiple sclerosis, uveoretinitis, thyreoiditis, Crohn's disease, insulin dependent diabetes mellitus, eczema, systemic lupus erythematosus and allogeneic graft rejection (e.g. rejection of allogeneic skin, kidney, heart, liver or lung transplants). The term "eczema" relates, in particular, to eczema due to delayed type hypersensitivity. The term "treatment" or "treating" includes preventive and/or therapeutic treatments.

9-cis retinoic acid and its derivatives and metabolic precursors and prodrugs as well as metabolites of 9-cis retinoic acid when administered to patients are effective, in particular in the therapy of the following T-helper cell type 1 (Th1) mediated diseases: rheumatoid arthritis, multiple sclerosis, uveoretinitis, thyreoiditis, Crohn's disease, insulin dependent diabetes mellitus, systemic lupus erythematosus as well as eczema with its various classes of exogenous eczema, such as irritant dermatitis, allergic contact dermatitis, tylotic eczema or pompholyx, endogenous eczema, such as seborrheic eczema (also called seborrhoic dermatitis or seborrheic dermatitis), asteatotic eczema and discoid eczema, and eczemas localised at various sites of the body. 9-cis retinoic acid and its derivatives and metabolic precursors and prodrugs are effective in all those immune diseases which might be somehow linked with an increase of Th1 cell activity and an increased secretion of the related cytokines interleukin-12, interleukin-2, interferon γ and tumor necrosis factor α, β.

For the treatment of Th1 mediated diseases other than eczema, the active compound, i.e. 9-cis retinoic acid, a pharmaceutically acceptable salt or a pharmaceutically acceptable hydrolyzable ester thereof, 9-cis retinal or a pharmaceutically acceptable acetal thereof or 9-cis retinol or a pharmaceutically acceptable hydrolyzable ester thereof or metabolites of 9-cis retinoic acid, is administered orally. For the treatment of eczema the active compound is administered either orally or topically. Preferably, said compound is administered as a composition containing said active compound and a pharmaceutically acceptable carrier or diluent compatible with said active compound. In preparing such composition, any conventional pharmaceutically acceptable carrier can be utilized. When the drug is administered orally, it is generally administered at regular intervals, conveniently at mealtimes or once daily. It has been established that this compound is effective in doses which show no or only mild side effects when given orally or when given topically. Therefore, oral administration of the active compound is generally preferred. For treating eczema however topical administration may also be used advantageously.

In the treatment of T-helper cell type 1 mediated immune diseases, 9-cis retinoic acid and its derivatives and metabolic precursors and prodrugs as well as its metabolites, when administered orally, are therapeutically efficacious in doses which induce no adverse events or only such mild side effect as dry lips and transient headache. At present, all retinoids exerting therapeutic effects in dermatological and oncological indications have to be administered orally in doses which induce more or less marked side effects, belonging to the toxic syndrome of hypervitaminosis A, such as mucocutaneous, musculoskeletal and neurologic manifestations, particularly headache. In addition, they produce laboratory abnormalities such as elevated transaminases (ALAT, ASAT), elevated alkaline phosphatase, as well as elevated triglycerides and cholesterol. In contrast, the daily doses of 9-cis retinoic acid and its derivatives and metabolic precursors and prodrugs and metabolites of 9-cis retinoic acid (typically 20 to 60 mg) therapeutically efficacious in T-helper cell type 1 mediated immune diseases produce only very slight side effects, such as dry lips and transient headache, whereas all the other toxic signs and symptoms of the hypervitaminosis A syndrome, including the laboratory abnormalities, were not induced.

These same low daily doses of 9-cis retinoic acid, however, had no therapeutic effect on non-malignant skin-disorders, such as acne, psoriasis, lamellar ichthyosis, Darier's disease and lichen planus. In summary, it was found that the very well tolerated low daily doses of 20 to 60 mg of 9-cis retinoic acid (and its derivatives and metabolic precursors and prodrugs) are efficacious in the treatment of T-helper cell type 1 mediated immune diseases, whereas such doses are not efficacious in the treatment of non-malignant skin disorders, such as acne, psoriasis and other keratinizing dermatoses. In malignant skin diseases and solid tumors of other organs, even high oral daily doses of 9-cis retinoic acid of up to 300 mg, inducing marked to severe side effects, did not lead to major objective tumor regressions.

In the treatment of T-helper cell type 1 mediated immune diseases, 9-cis retinoic acid, a pharmaceutically acceptable salt or a pharmaceutically acceptable hydrolyzable ester thereof, 9-cis retinal or a pharmaceutically acceptable acetal thereof or 9-cis retinol or a Pharmaceutically acceptable hydrolyzable ester thereof or metabolites of 9-cis retinoic acid can be used alone or in combination with other measures, e.g. in combination with other pharmaceutically active substances such as topical or systemic corticosteroids and other immunosuppressive agents (cytostatics, antimetabolites, biological response modifiers, e.g. interferons, interleukins and other cytokines). If used in combination with other substances, 9-cis retinoic acid or its derivative or metabolic precursor or prodrug or its metabolites and said other substance can be administered separately or, preferably, incorporated in effective amounts into one pharmaceutical composition.

In the scope of the present invention, the "pharmaceutically acceptable salts" includes any salt chemically permissible in the art for 9-cis retinoic acid and applicable to human patients in a pharmaceutically acceptable preparation. Any such conventional pharmaceutically acceptable salt of 9-cis retinoic acid can be utilized. Among the conventional salts which can be utilized there are the base salts included, for example, alkali metal salts such as the sodium or potassium salt, alkaline earth metal salts such as the calcium or magnesium salt, and ammonium or alkyl ammonium salts.

In accordance with this invention the 9-cis retinoic acid can also be administered in the form of its pharmaceutically acceptable hydrolyzable esters. Any pharmaceutically acceptable hydrolyzable ester can be used in the compositions and methods of this invention. Among the preferred esters are: the aromatic esters such as benzyl esters in which the benzyl moiety is unsubstituted or substituted with lower alkyl, halo, nitro, thio, or substituted thio; or lower alkyl esters, e.g. ethyl, t-butyl, cyclopentyl, cyclohexyl or cycloheptyl ester; or 9-fluorenylmethyl ester.

In the scope of the present invention the term "alkyl" means straight-chain, branched or cyclic alkyl residues, in particular those containing from 1 to 12 carbon atoms, such as methyl, ethyl, propyl, isopropyl, t-butyl, decyl, dodecyl, cyclopentyl, cyclohexyl, cycloheptyl and the like. The term "lower alkyl" means alkyl groups containing from 1 to 7 carbon atoms.

In accordance with this invention a metabolic precursor or prodrug of 9-cis retinoic acid or metabolites of 9-cis retinoic acid are, in particular, 9-cis retinal, 9-cis retinol, a pharmaceutically acceptable acetal of 9-cis retinal or a pharmaceutically acceptable hydrolyzable esters of 9-cis retinol can alternatively be used instead of 9-cis retinoic acid, and any pharmaceutically acceptable acetal of 9-cis retinal and any pharmaceutically acceptable hydrolyzable ester of 9-cis retinol or 4-oxo-9-cis retinoic acid can be used in the compositions and methods of this invention. Among the preferred acetals of retinal are dialkyl acetals, especially di(lower alkyl) acetals such as the diethyl acetal, and dibenzyl acetals, wherein the benzyl moieties are unsubstituted or substituted with is lower alkyl, halo, nitro, thio or substituted thio. Among the preferred hydrolyzable esters of 9-cis retinol are the esters formed with $C_1$–$C_{20}$-carboxylic acids such as $C_1$–$C_{20}$-alkanoic acids and $C_1$–$C_{20}$-alkenoic acids; particularly preferred are those carboxylic acid esters which contain and even number of carbon atoms in the carboxylic acid moiety such as acetate, stearate or palmitate.

The aforementioned 9-cis retinoic acid and its salts, its esters and its metabolic precursors or prodrugs as well as its metabolites are useful especially in pharmaceutically acceptable oral or topical modes. These pharmaceutical compositions contain said active compound in association with a compatible pharmaceutically acceptable carrier material. Any conventional carrier material can be utilized. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavouring agents, preservatives, stabilizers, emulsifying agents, buffers and the like may be added in accordance with accepted practices of pharmaceutical compounding.

The pharmaceutical preparations can be made up in any conventional form including inter alia: (a) a solid form for oral administration such as tablets, capsules (e.g. hard or soft gelatine capsules), pills, sachets, powders, granules, and the like; and (b) preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

For topical administration to the skin or mucous membrane the aforementioned derivative is preferably prepared as ointments, tinctures, creams, gels, solution, lotions, sprays, suspensions, shampoos, hair soaps, perfumes and the like. In fact, any conventional composition can be utilized in this invention. Among the preferred methods of applying the composition containing the agents of this invention is in the form of an ointment, cream or lotion. The pharmaceutical preparation for topical administration to the skin can be prepared by mixing the aforementioned active ingredient with non-toxic, therapeutically inert, solid or liquid carriers customarily used in such preparation. These preparations generally contain at least about 0.0005 percent by weight, preferably 0.0005 to 0.05 and more preferably about 0.001 to 0.01 percent by weight, of the active ingredient (i.e. 9-cis retinoic acid or its derivative or its metabolic precursor or prodrug or metabolites) based upon the total weight of the composition. Since toxicity and irritancy of the active ingredient varies, depending on the kind of tissue—normal or pathologically altered—on which it is applied, it may however often be used in topical compositions in amounts up to 0.15 percent by weight or even higher amounts. It is also preferred to apply these preparations once or twice daily to the skin. These preparations can be applied according to the need of the patient. In carrying out this invention, the active ingredient can be applied in an aqueous solution or an alcohol solution such as ethanol.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-α-tocpherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, ethylene glykol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid containing at least about 14 carbon atoms. Also, conventional perfumes and lotions generally utilized in topical perparation for the hair can be utilized in accordance with this invention. Furthermore, if desired, conventional emulsifying agents can be utilized in the topical preparations of this invention.

A preferred oral dosage form comprises tablets, pills, sachets, or capsules of hard or soft gelatin, methylcellulose or of another suitable material easily dissolved in the digestive tract. Each tablet, pill, sachet or capsule can preferably contain from about 5 to about 50 mg, more preferably from about 10 to about 20 mg, of active ingredient. The oral dosages contemplated in accordance with the present invention will vary in accordance with the needs of the individual patient as determined by the prescribing physician. Generally, however, a daily dosage of from about 0.05 mg to about 1.5 mg per kg of body weight and preferably from about 0.3 mg to about 0.9 mg per kg of body weight of the patient is utilized. This dosage may be administered according to any dosage schedule determined by the physician in accordance with the requirements of the patient.

Oral daily doses of from about 0.05 mg to about 1.5 mg per kg of body weight and preferably from about 0.3 mg to about 0.9 mg per kg of body weight are administered either continuously or on an intermittent schedule e.g. in repetitive cycles of weekly 3 days on-, and 4 days off-treatment, or in cycles of alternatively 7 days on-, and 7 days off-treatment. For maintenance of a sufficiently high blood plasma or tissue level, it can be necessary to avoid concomitant medication of P450 isoenzyme inducers and/or to add inhibitors of P450 isoenzymes. Dosage schedules are dependent on the kind of Th1-mediated immune disease such as e.g. eczema, rheumatoid arthritis, multiple sclerosis or Crohn's disease, but also on the stage of disease, plasma and tissue levels of 9-cis retinoic acid, concomitant drug therapy and the patients' condition. 9-cis retinoic acid therapy can be given as continuous daily treatment or on an intermittent schedule as described above. 9-cis retinoic acid therapy can also consist in a continuous treatment as an induction therapy, until a remission is achieved, and followed subsequently by a treatment on an intermittent schedule as a maintenance therapy.

9-cis retinoic acid treatment can be combined with other drugs used for treatment of Th1-mediated diseases, such as e.g. rheumatoid arthritis, multiple sclerosis or Crohn's disease. Such drugs are e.g. methotrexate, azathioprim, corticosteroids, cyclosporin, mycophenolic mofetil or interferons e.g. interferon β.

The dosage for treatment typically depends on the route of administration, the age, weight and disease condition of the individual. Suitable dosage forms are known in the art or can be easily obtained in a manner known per se. Formulations of lotions, gels, creams, hard or soft gelatin capsules, tablets and sachets that are particularly suitable in the scope of the present invention or that can be easily adjusted in accordance with the above teaching are disclosed e.g. in U.S. Pat. No. 5,428,071.

In a preferred embodiment, the treatment of eczematoid conditions is carried out orally or topically.

In one embodiment, this invention provides a method of treating an eczematoid condition in a human patient afflicted with the condition, comprising orally administering or delivering to said patient 9-cis retinoic acid in an amount effective to treat the condition in said patient. A patient having active eczema is treated to lessen the severity of the eczema lesions or other symptoms. In the case where a patient previously had active eczema lesions, which have been brought into remission, this invention provides prophylactic treatment against the recurrence of active manifestations of eczema. In accordance with this invention, any eczematoid condition can be treated by the described method. Examples of the active or remission state eczematoid conditions which are treated include acute and chronic irritant dermatitis, allergic contact dermatitis, tylotic eczema or pompholyx, seborrhoic eczema, asteatotic eczema, and discoid eczema.

9-cis retinoic acid can be administered orally in any amount which is effective to treat the eczematoid condition, for example, the 9-cis retinoic acid or a precursor thereof which delivers from about 0.3 to about 0.9 milligrams of 9-cis retinoic acid per kilogram of body weight is preferred. This dosage may be administered according to any dosage schedule determined by the physician in accordance with the requirements of the patient. In accordance with specific embodiments, oral daily doses from about 0.3 mg to about 0.9 mg per kg of body weight are administered either continuously or on an intermittent schedule e.g. in repetitive cycles of weekly 3 days on-, and 4 days off-treatment, or in cycles of alternatively 7 days on-, and 7 days off-treatment. 9-cis retinoic acid therapy can also consist in a continuous treatment as an induction therapy, until a remission is achieved, and followed subsequently by a treatment on an intermittent schedule as a maintenance therapy.

For treatment of eczematoid conditions by oral delivery of 9-cis retinoic acid, the 9-cis retinoic acid is delivered by administering orally to the patient a composition comprising 9-cis retinoic acid or a precursor thereof which delivers or produces 9-cis retinoic acid. Examples of suitable precursors of 9-cis retinoic aced include pharmaceutically acceptable salts of 9-cis retinoic acid, hydrolyzable esters of 9-cis retinoic acid, 9-cis retinal, hydrolyzable esters 9-cis retinal, 9-cis retinol, and hydrolyzable esters of 9-cis retinol.

In an embodiment of the method of oral treatment of eczematoid conditions, the composition containing 9-cis retinoic acid or precursor thereof is present in an oral unit dosage form. In a more specific embodiment the oral unit dosage form is a tablet, capsule, pill or sachet containing from five to fifty milligrams, preferably from 10 to 20 mg of 9-cis retinoic acid or a pharmaceutically acceptable salt or hydrolyzable ester thereof.

The pharmaceutically acceptable salts include any salt chemically permissible for 9-cis retinoic acid and applicable to human patients in a pharmaceutically acceptable preparation. Any conventional pharmaceutically acceptable salt of 9-cis retinoic acid can be utilized. Among the conventional salts which can be utilized are included the base salts, for example, alkali metal salts such as sodium or potassium, alkaline earth metal salts such as calcium or magnesium, and ammonium or alkyl ammonium salts.

Pharmaceutically acceptable hydrolyzable esters can be used in the compositions and method of this invention. Among the esters are the aromatic esters such as benzyl (OBzl) or benzyl substituted with lower alkyl, halo, nitro, thio, or substituted thio, i.e., lower alkyl (1–7 carbon atoms) thio; aliphatic esters such as lower alkyl, t-butyl, cyclopentyl, cyclohexyl, cycloheptyl, and 9-fluorenylmethyl.

In another embodiment, this invention provides a method of treating an eczematoid condition of the skin in a human patient in need of such treatment, comprising topically applying to the area of the skin of said patient subject to the condition 9-cis retinoic acid in an amount effective to alleviate the effects of the condition. A patient having active eczema is treated to lessen the severity of the eczema lesions or other symptoms. In the case where a patient previously had active eczema lesions, which have been brought into remission, this invention provides prophylactic treatment against the recurrence of active manifestations of eczema. In accordance with this invention, any eczematoid condition can be treated by the described method. Examples of the active or remission state eczematoid conditions which are treated include irritant dermatitis, allergic contact dermatitis, tylotic eczema or pompholyx, seborrhoic eczema, asteatotic eczema, and discoid eczema.

For treatment of eczematoid conditions by topical delivery of 9-cis retinoic acid, the 9-cis retinoic acid is delivered by administering topically to the patient a topical composition comprising a compound selected from 9-cis retinoic acid and dermatologically acceptable salts thereof. In formulating these topical compositions, the compound of formula I, its pharmaceutically acceptable salts or its pharmaceutically acceptable esters are admixed with a pharmaceutically acceptable carrier for topical administration. Any conventional pharmalceutically acceptable carrier can be utilized in accordance with this invention.

These topical compositions which contain 9-cis retinoic acid as well as its salts can contain any of the conventional excipients and additives commonly used in preparing topical compositions. Among the conventional additives or excipients which can be utilized in preparing these compositions in accordance with this invention are preservatives, thickeners, perfumes and the like. In addition, the conventional antioxidants, such as butylated hydroxyanisoles (BHA), ascorbyl palmitate, propyl gallate, citric acid, butylated hydroxytoluene (BHT), ethoxyquin, tocopherol, and the like can be incorporated into these compositions. These topical compositions can contain conventional acceptable carriers for topical applications which are generally utilized in these compositions. These compositions may contain thickening agents, humectants, emulsifying agents and viscosity stabilizers, such as those generally utilized. In addition, these compositions can contain colorants and perfumes which are conventional in preparing cosmetic compositions.

The composition for topical administration can contain any concentration of 9-cis retinoic acid or a salt thereof which is effective to treat the eczematoid condition. For example, a composition which contains the compound in a concentration from about 0.001 to about 0.05 percent by weight of the composition can be used. More specific concentrations of the compound which are suitable in the method include from about 0.003 to about 0.03 percent by weight of the composition; and from about 0.005 to about 0.01 percent by weight of the composition. Other suitable concentrations of the compound are at least about 0.0005 percent by weight; 0.0005 to 0.15 percent by weight; 0.0005 to 0.05 percent by weight; and 0.001 to 0.01 percent by weight of the composition.

The pharmaceutically acceptable salts include any salt chemically permissible for 9-cis retinoic acid and applicable to human patients in a pharmaceutically acceptable preparation. Any conventional pharmaceutically acceptable salt of 9-cis retinoic acid can be utilized. Among the conventional salts which can be utilized are included the base salts, for example, alkali metal salts such as sodium or potassium, alkaline earth metal salts such as calcium or magnesium, and ammonium or alkyl ammonium salts.

The topical composition of may be in any form which is conventional for topical compositions. For example, the topical composition can be present in the form of an ointment, cream, gel, lotion, or shampoo. Other examples of suitable forms for the topical composition include tinctures, solutions, suspensions, micronized powders, suspensions, soaps, perfumes and aerosols.

The invention will be better understood from the following example, which is illustrative of the invention and not limiting.

EXAMPLE 1

Activity of 9-cis Retinoic Acid in Chronic Hand Eczema a) Methods

Fifteen patients, eight men and seven women, with chronic hand eczema, refractory to conventional treatment, were treated with 9-cis retinoic acid. Their mean age was 52.3 years, range 21–83. Before the start of 9-cis retinoic acid therapy, their eczema had already lasted for 3 months to 8 years, with a mean of 29 months. Besides avoidance of irritants and allergens, their previous treatment consisted in topical topical corticosteroids (15 patients), topical tar (2 patients), isotretinoin (2 patients), tretinoin (1 patient) and X-rays (3 patients). The response to these treatments was in all cases unsatisfactory, in 4 patients moderate in 3 patients slight and in 8 patients no response at all. Therapy consisted in a once daily oral dose of 40 mg 9-cis retinoic acid, given in the form of two soft gelatin capsules containing 20 mg of 9-cis retinoic acid each, with breakfast. 8 patients received in the first week only 20 mg. Mean duration of treatment was 2 months, range 1–3 months. The following lesions and symptoms were recorded on a 0–4 scale (0=none, 1=mild, 2=moderate and 4=severe) and used for evaluating the therapeutic effect: Erythema, papules and vesicles, desquamation, hyperkeratosis, rhagades and pruritus/pain. Side effects, particularly those belonging to the hypervitaminosis A syndrome, were recorded: Headache, dry lips, other mucocutaneous manifestations, muscoskeletal symptoms and laboratory abnormalities.

b) Results

As can be seen from Table 1, all fifteen patients responded markedly to 9-cis retinoic acid (9-cis-RA) and all the various lesions and symptoms were improved by the treatment. The total lesion-symptom score of the 14 responding patients was reduced by a mean of 81.3% (range 53–100%). The various lesions and symptoms such as erythema, papules and vesicles etc., were all favouraboly influenced and regressed by 62–100%. 9-cis retinoic acid in a dose of 40 mg daily was very well tolerated. The only side effect noted in these 15 patients were transient headache in 2, and dry lips in 5 patients. No other mucocutaneous manifestations, seen with higher doses and no musculoskeletal or other symptoms were observed. Such symptoms were seen with higher doses [Kurie et al., Clin. Cancer Res. 2, 287–293 (1996); Miller et al., Clin. Cancer Res. 2, 471–475 (1996)]. The well known laboratory abnormalities, such as elevation of transaminases (ALAT, ASAT) alkaline phosphatase, triglycerides and cholesterol, frequently caused by retinoids were not seen with this low dosage of 9-cis retinoic acid. The response to the therapy with 9-cis retinoic acid in patients chronic hand eczema, refractory to conventional treatment, was assessed by the doctor, as well as by the patient and was considered as very good or good in 13 of 15 patients or 87% of the patients (Tables 1 and 2).

TABLE 1

Treatment of Chronic Hand Eczema with 9-cis Retinoic Acid

| | Patient No. | | | | | | |
|---|---|---|---|---|---|---|---|
| | 1 | 2 | 3 | 4 | 5 | 6 | 7 |
| Sex | f | m | m | m | m | m | f |
| Age (years) | 83 | 41 | 49 | 50 | 37 | 43 | 78 |
| Duration of eczema (months) | 3 | 20 | 16 | 60 | 36 | 24 | 36 |
| Previous treatment | top. steroids | top. steroids | top. steroids x-rays | tops. steroids | top. steroids | top. steroids isotretinoin tretinoin, acitretin | top. steroids x-rays |
| Response to previous treatment | no | slight | moderate | moderate | moderate | no | no |
| 9-cis RA | | | | | | | |
| Oral daily dose (mg) | 40 | 40 | 40 | 40 | 40 | 40 | 40 |
| Duration of treatment (months) | 2 | 2 | 2 | 3 | 1 | 2 | 3 |
| Efficacy (0–4 scale) before/after treatment | | | | | | | |
| Erythema | 1/0 | 1.0 | 1/0.5 | 1/0.5 | 2/0 | 1/0 | 2/0 |
| Papules, vesicles | 3/0 | 3/1 | 2/1 | 2/1 | 2/0 | 1/0 | 0/0 |
| Pruritus (+ pain) | 2/0 | 2/0 | 3/1 | 3/1 | 3/2 | 4/0 | 5/0 |
| Desquamation | 2/1 | 3/1 | 3/1 | 3/1 | 2/1 | 1/0 | 3/0 |
| Hyperkeratosis | 4/0 | 3/0 | 1/1 | 2/1 | 1/0 | 2/0 | 1/0 |
| Rhagades | 3/0 | 2/0 | 1/0 | 0.5/0 | 1/0 | 1/0 | 3/0 |
| Total Score (0–4 scale) | 15/1 | 14/2 | 11/4.5 | 11/4.5 | 11/3 | 10/0 | 14/0 |
| Reduction of score in % | 93 | 86 | 59 | 61 | 74 | 100 | 100 |
| Response assessed by patient | very good | very good | good | very good | very good | very good | very good |
| Response assessed by doctor | very good | very good | good | good | good | very good | very good |

| | Patient No. | | | | | | | |
|---|---|---|---|---|---|---|---|---|
| | 8 | 9 | 10 | 11 | 12 | 13 | 14 | 15 |
| Sex | m | m | f | f | f | f | m | f |
| Age (years) | 62 | 53 | 51 | 66 | 49 | 50 | 51 | 21 |
| Duration of eczema (months) | 96 | 6 | 48 | 48 | 12 | 48 | 18 | 8 |
| Previous treatment | top. steroids | top. steroids | top. steroids isotretinoin | top. steroids | top. steroids | top. steroids tar | top. steroids | top. steroids |
| Response to previous treatment | slight | no | no | slight | no | no | no | moderate |
| 9-cis RA | | | | | | | | |
| Oral daily dose (mg) | 40 | 40 | 40 | 40 | 40 | 40 | 40 | 40 |
| Duration of treatment (months) | 2 | 2.5 | 1.5 | 1.5 | 2 | 2.5 | 1 | 2 |
| Efficacy (0–4 scale) before/after treatment | | | | | | | | |
| Erythema | 4/2 | 0/0 | 2/2 | 2/0 | 1/0 | 1/0 | 2/1 | 1/0 |
| Papules, vesicles | 3/1 | 0/0 | 0/0 | 1/0 | 0/0 | 0/0 | 0/0 | 1/0.5 |
| Pruritus (+ pain) | 5/2 | 4/1 | 7/7 | 4/0 | 5/0 | 5/0.5 | 3/1 | 2/0.5 |
| Desquamation | 1/0 | 1/0 | 3/3 | 2/0 | 0/0 | 0/0 | 2/0 | 1/0.5 |

TABLE 1-continued

Treatment of Chronic Hand Eczema with 9-cis Retinoic Acid

| Hyperkeratosis | 1/1 | 2/0 | 3/3 | 2/1 | 2/0 | 2/0.5 | 2/0 | 2/0.5 |
|---|---|---|---|---|---|---|---|---|
| Rhagades | 3/2 | 2/0 | 2/2 | 2/1 | 2/0 | 1/0 | 2/0 | 1/0 |
| Total Score (0–4 scale) | 17/8 | 9/1 | 17/17 | 13/2 | 10/0 | 9/1 | 11/2 | 8/2 |
| Reduction of score in % | 53 | 89 | 0 | 85 | 100 | 89 | 82 | 75 |
| Response assessed by patient | moderate | very good | no | very good | very good | good | very good | good |
| Response assessed by doctor | good | very good | no | good | very good | good | good | moderate |

TABLE 2

Therapy with oral 9-cis Retinoic Acid (9-cis RA) In Chronic Hand Eczema (Summary)

| No. of patients | 15 |
|---|---|
| Sex | 8 males, 7 females |
| Age | 21–83 years, mean 52.3 years |
| Duration of eczema | 3–96 months, mean 29 months |
| Previous treatment | topical corticosteroids (15), tar (2), isotretinoin (2), tretinoin (1), acitretin (1) |
| Response to previous treatment | moderate (4), slight (3), no (8) |
| 9-cis RA Therapy | |
| Daily oral dose | 40 mg |
| Duration of treatment | 1–3 months, mean 2 months |
| Efficacy | |
| Reduction of Lesion/ symptom score, in % | for all 15 patients 0–100, mean 76.3 for the 14 responding patients 53–100, mean 81.8 |

| | Assessment by | |
|---|---|---|
| Response of patients to 9-cis RA therapy | Patient | Doctor |
| very good | 10 (67%) | 6 (40%) |
| good | 3 (20%) | 7 (47%) |
| moderate | 1 (6.5%) | 1 (6.5%) |
| slight | 0 (0%) | 0 (0%) |
| no | 1 (6.5%) | 1 (6.5%) |
| Side effects | | |
| Dry lips | 5 (33.3%) | |
| Headache, transient | 2 (13.3%) | |

What is claimed is:

1. A method of treating chronic hand eczema in a human patient in need of treatment, comprising orally administering to said patient at least one unit oral dosage form of 9-cis retinoic acid or a pharmaceutically acceptable salt or hydrolyzable ester thereof, in an effective amount of from 0.05 to 1.5 milligrams per kilogram body weight per day.

2. The method according to claim 1, wherein said patient manifests eczema lesions.

3. The method according to claim 1, wherein said treatment is prophylactic to eczema lesions which are in remission.

4. The method according to claim 1, wherein said patient is afflicted with continual or recurrent hand eczema lesions for at least three months.

5. The method according to claim 1, wherein said effective amount administered is from 0.3 to 0.9 milligrams per kilogram body weight per day.

6. The method according to claim 1, wherein said effective amount administered is from twenty to sixty milligrams per day.

7. The method according to claim 6, wherein said effective amount administered is about forty milligrams per day.

8. The method according to claim 1, wherein said at least one unit oral dosage form administered is from twenty to sixty milligrams of 9-cis retinoic acid or a pharmaceutically acceptable salt or hydrolyzable ester thereof.

* * * * *